United States Patent [19]

Ellis

[11] 4,019,510
[45] Apr. 26, 1977

[54] THERAPEUTIC METHOD OF USING LOW INTENSITY DIRECT CURRENT GENERATOR WITH POLARITY REVERSAL

[75] Inventor: Franklin Hammond Ellis, Rochester, N.Y.

[73] Assignee: Sybron Corporation, Rochester, N.Y.

[22] Filed: Feb. 10, 1975

[21] Appl. No.: 548,352

[52] U.S. Cl. .............................. 128/172.1; 128/421
[51] Int. Cl.² .......................................... A61N 1/36
[58] Field of Search .............. 128/172.1, 362, 404, 128/419 R, 421–423

[56] References Cited
UNITED STATES PATENTS

| | | | |
|---|---|---|---|
| 2,121,875 | 6/1938 | Kruse et al. | 128/362 |
| 2,126,070 | 8/1938 | Wappler | 128/172.1 |
| 2,355,231 | 8/1944 | Moore | 128/172.1 |
| 3,563,247 | 2/1971 | Bowers | 128/422 |
| 3,727,616 | 4/1973 | Lenzkes | 128/422 |
| 3,893,462 | 7/1975 | Manning | 128/421 |
| 3,918,459 | 11/1975 | Horn | 128/419 R |

FOREIGN PATENTS OR APPLICATIONS 707,011 3/1965 Canada .................. 128/419 R

OTHER PUBLICATIONS

Spadaro et al, "Antibacterial Effects of Silver with Weak Direct Current", Antibac. Agents & Chemo., Nov. 1974, pp. 637–642, vol. 6, No. 5.

Primary Examiner—Robert W. Michell
Assistant Examiner—Lee S. Cohen
Attorney, Agent, or Firm—Theodore B. Roessel; J. Stephen Yeo

[57] ABSTRACT

A method for treating skin ulcers, infections and the like by eletrotherapy. Therapeutic low intensity direct current is applied to a patient by electrodes, at least one of which contains silver. The polarity of the direct current is reversed from time to time to prevent the accumulation of unwanted material upon the silver bearing electrode due to electrochemical action.

2 Claims, 2 Drawing Figures

THERAPEUTIC METHOD OF USING LOW INTENSITY DIRECT CURRENT GENERATOR WITH POLARITY REVERSAL

BACKGROUND OF THE INVENTION

This invention relates generally to low intensity direct current treatment of skin ulcers and the like.

It is known that the healing of various skin lesions and ulcers may be accelerated by electrotherapy techniques involving the application of low intensity direct current through electrodes attached to the area adjacent to the pathologic tissue. Low intensity direct current (LIDC) Generators are known which regulate the current flow so that healing is promoted. In a copending U.S. application Ser. No. 545,609, filed Jan. 30, 1975, by Franklin H. Ellis et al, for "Electrode Having Antiseptic Properties for LIDC Therapy Use", now U.S. Pat. No. 3,964,477, it is disclosed that the use of a silver or silver bearing material in the construction of the positive electrode further aids the healing process by providing a bactericidal effect. One explanation of this effect is that positive silver ions are formed which chemically bind with the DNA molecules of the bacteria and prevent reproduction thereof. However, LIDC causes electrode contamination if applied continuously while maintaining a given polarity of LIDC flow. In particular, it has been found that the positive silver electrode gradually becomes contaminated by a coating of broken proteins formed by electrochemical action. The resultant effects are the reduction of positive silver ions and the increase of electrical resistance between the positive electrode and the patient. It is, therefore, desirable, and an object of my invention to provide means and method for applying low intensity direct current without the detrimental effect of electrical polarization.

SUMMARY OF THE INVENTION

In accordance with the invention apparatus is provided for applying direct current to a pair of electrodes at least one of which contains silver. The apparatus includes at least one current source which applies direct current through the electrodes for part of a time cycle. A second current source may apply direct current of reversed polarity for the remainder of the cycle. Actuation or selection of the current source is accomplished by suitable control means.

DETAILED DESCRIPTION OF THE DRAWINGS

According to the present invention I have found that by providing a positive current flow from a silver electrode for a first time period and a negative current flow for a second time period reduces the effects of silver electrode polarization without substantially reversing the beneficial effects of the therapy. Different time periods and/or currents may be chosen to optimize the therapeutic results of the low intensity direct current. Two examples of time and current cycles which have proven satisfactory are: (1) a positive current of 4 microamps for 50-minutes, followed by a negative current of 250 microamps for 5 minutes; and (2) a positive current of 250 microamp for 5 minutes followed by zero current for 55 minutes. Both of these cycles have been found to provide the desired healing effects while avoiding polarization of the electrodes. The circuitry to be hereafter described will be directed to the former cycle but with obvious modification it can be adapted to provide a number of other cycles, including the latter.

Materials which tend to contaminate the silver electrodes during positive current flow are freed during negative current flow. The wound is occasionally swabbed to cleanse it of the freed materials and the electrodes replaced.

Figure 1:
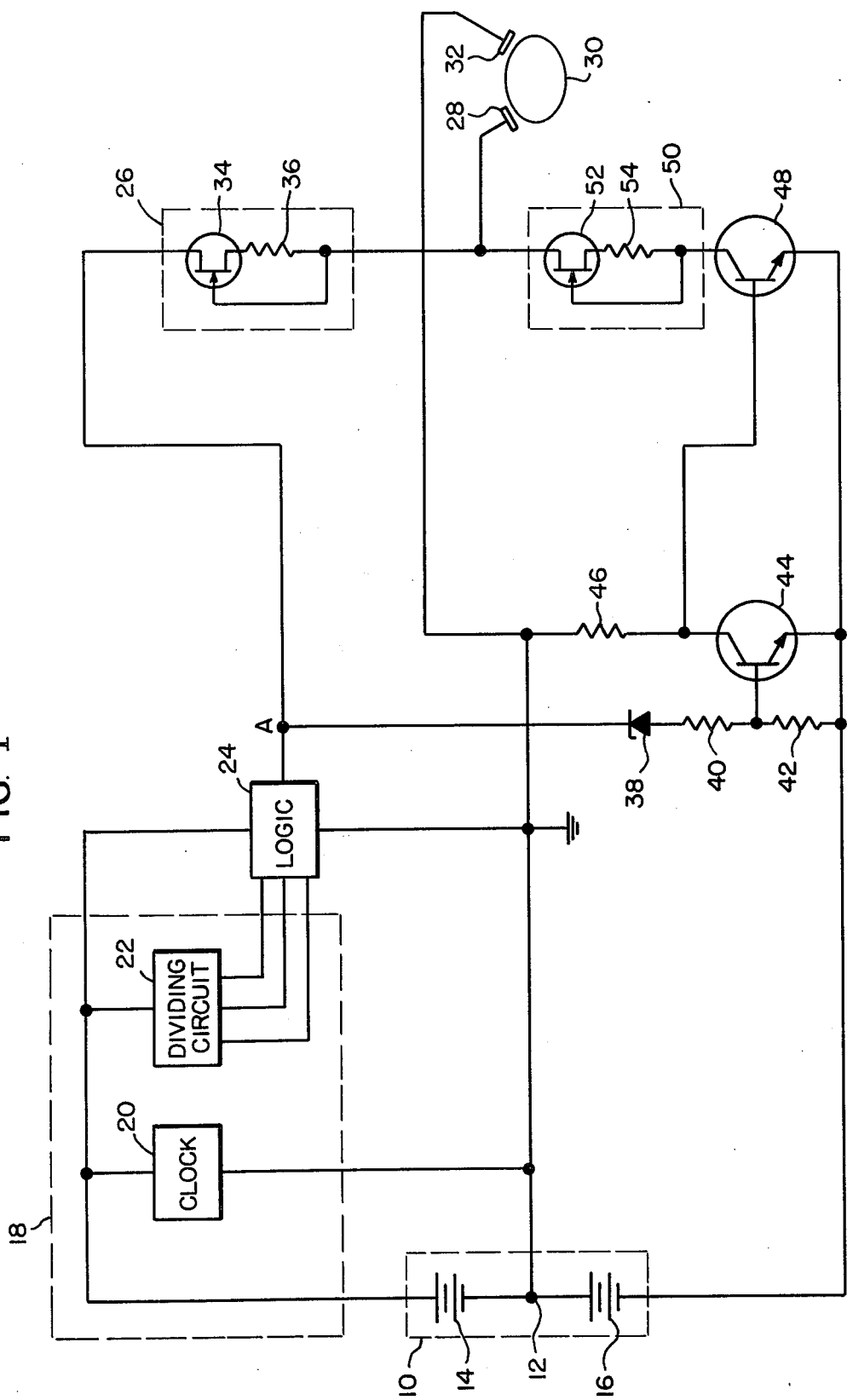
FIG. 1 is a schematic diagram of form of circuitry suitable for practicing the present invention.

In the preferred emodiment shown in FIG. 1 a low intensity reversible direct current generator includes a battery 10. The battery 10 may have eight 1.2 volt cells and be of the nickel cadium rechargable type with a tap 12 between the fourth and fifth cells to provide positive and negative 4.8 volt sources 14 and 16 respectively. The positive 4.8 volt source 14 powers a timing means 18, which may include a clock 20 or a pulse generator for producing repetitive pulses having a cycle of 1 second, and a divider circuit 22 for dividing the number pulses produced by clock 20.

The dividing circuit 22 has outputs representative of a first time period and a second time period, which define a time cycle. The clock 20, and the dividing current will be discussed further later in the description.

The output of the timing circuit 18 controls a logic circuit 24 which generates an output voltage for the duration of the first time period and is off during the second time period. The logic circuit 24 is also described in detail later in the description.

During the first time period, the logic circuit 24 has an output voltage substantially that of positive source 14 referred to the center tap 12. The output voltage is applied to a first current regulator circuit 26 for maintaining a constant current flow through a first electrode 28 attached to the patient 30. The current passes through the patient, to a second electrode 32, and returns therefrom to center tap 12 of the battery 10.

For the duration of the first time period, the current is positive at the first electrode 28 and the magnitude of the current is determined by first current regulator 26. The first electrode is preferably constructed of silver or silver bearing material for bactericidal effects.

The current regulator 26 may be a conventional current regulator. One embodiment uses a field effect transistor 34 in series with a resistor 36. The gate of the field effect transistor 34 is controlled by a voltage developed across the series resistor 36. Current intensity is determined by the value of the series resistor 36. Alternatively, regulator 26 may take the form of a zener diode current regulator or another type of regulator known in the art.

The output of the logic circuit 24 is connected in series through a 51 volt zener diode 38 and a pair of biasing resistors 40, 42 to battery 10 so that the total battery voltage of 9.6 volts appears across zener 38 and resistors 40 and 42 during the first time period. The zener is reversed biased so as to maintain a constant voltage of 4.5 v across the resistors 40 and 42.

The biasing resistors 40, 42 bias the base of a transistor 44 which turns on and maintains an on condition during the first time period. The collector of transistor 44 is connected through a resistor 46 to the center tap 12 of battery 10 and to the base of a second transistor 48. Transistor 48 is arranged to act as a switch for a second current regulator circuit 50.

After the expiration of the first time period, the voltage at the output of the logic circuit 24 is reduced to zero. Transistor 44 loses its bias current and is turned off, allowing the current from resistor 46 to pass through the base and the emitter of transistor 48 thereby turning transistor 48 on. This completes a current path consisting of section 16 of battery 10 through electrode 32 and electrode 28 and continuing through second current regulator 50.

During the second time period, the current magnitude is determined by the second current regulator circuit 50. This regulator may also take the form of field effect transistor 52 with a series resistor 54, the current being determined by the series resistor 54.

It is to be noted that during the second time period the polarity of the current across the electrodes 28 and 32 is opposite to the polarity of the current thereacross during the first time period. This reversed current condition exists during the second time period.

The first and second time periods repeat indefinitely, causing the current to flow first in one direction for a first time period and then in the opposite direction for a second time period.

Figure 2:
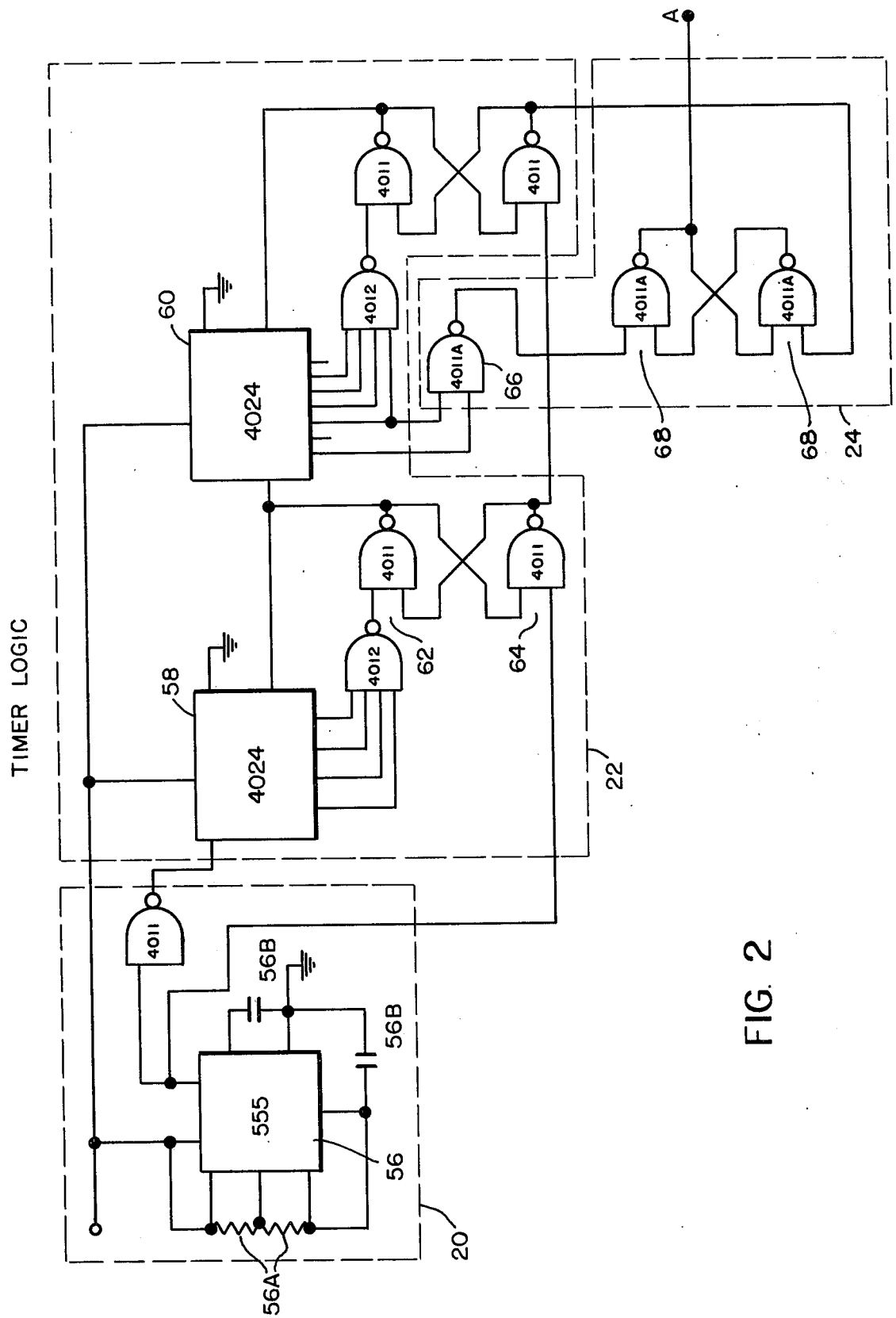
FIG. 2 shows a detail some of the circuitry of FIG. 1.

Preferred circuitry of timing means 18 and logic circuit 24 is shown in FIG. 2. These circuits are well known in the electronic arts, said will be only briefly described.

Timing means 18 includes a clock or pulse sensor 20 for generating repetitive pulses and a divider circuit 22 for dividing the number of pulses generated.

The clock 20 may be constructed from a Signetics 555 timing circuit 56 arranged with external resistor 56A and capacitors 56B so as to generate a series of repetitive pulses. One pulse a second is suitable rate. The dividing circuit 22 includes two counters 58, 60 such as RCA Model CD 4024 A.

Selected outputs of the counters are connected to gates 62 and 64 arranged at R-S flip-flops. The first counter divides the number of pulses generated by clock 20 by 60. Pulses are thereby produced at the rate of 1 minute at the output of the first counter. The pulses are directed to the second counter 60 and also serve to reset the first counter 58. The second counter 60 is arranged to divide by 60 also and to reset at the rate of once an hour.

Logic circuit 24 includes an AND gate 66 which inputs are connected to the second counter 60. An R-S flip-flop 68 is used so as to produce a voltage starting at 55 minutes and lasting until the second counter is reset at 60 minutes. After 55 minutes the output of R-S flip-flop is reduced to zero for 5 minutes. The output of R-S flip-flop 68 is connected to current regulator 26 and the zener diode 38 previously described.

The exemplary apparatus described includes well-known circuitry. Many alternate circuit arrangements may be used and not depart from the scope of my invention as claimed. For example, both current regulators may be continually energized but with their outputs alternatively connected to the electrodes.

I claim:

1. A method of therapeutic healing skin lesions, ulcers, and the like, comprising the steps of:
   maintaining electrodes at least one of which is silver bearing in proximity to said skin lesions, ulcers, and the like;
   applying a first current flow of positive polarity having a first magnitude in the order of 4 microamps through said electrodes for a first period of time in the order of 50 minutes;
   applying a second current flow of negative polarity and having a second magnitude in the order of 250 microamps for a second period of time in the order of 5 minutes through said electrodes, and
   alternately repeating said applying steps for the duration of the therapy.

2. A method of theropeutic healing skin lesions, ulcers, and the like, comprising the steps of:
   maintaining electrodes at least one of which is silver bearing in proximity to said skin lesions, ulcers, and the like;
   applying a current flow of positive polarity having a magnitude in the order of 250 microamps through said electrodes for a first time period in the order of 5 minutes;
   abstaining from applying current for a second time period in the order of 55 minutes; and
   alternately repeating said applying and abstaining steps for the duration of the therapy.

* * * * *